(12) United States Patent
Cheng et al.

(10) Patent No.: US 12,213,708 B2
(45) Date of Patent: Feb. 4, 2025

(54) REMOTE CONTROL MODULE FOR ADJUSTABLE IMPLANTS

(71) Applicant: Nuvasive Specialized Orthopedics, Inc., San Diego, CA (US)

(72) Inventors: Shanbao Cheng, Aliso Viejo, CA (US); Jorge Lopez Camacho, Aliso Viejo, CA (US); Youngsam Bae, Aliso Viejo, CA (US); Michael Moeller, Aliso Viejo, CA (US); Gabriel Buenviaje, Aliso Viejo, CA (US); Shawn Placie, Aliso Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 286 days.

(21) Appl. No.: 17/405,663

(22) Filed: Aug. 18, 2021

(65) Prior Publication Data
US 2022/0071670 A1    Mar. 10, 2022

Related U.S. Application Data

(60) Provisional application No. 63/075,640, filed on Sep. 8, 2020.

(51) Int. Cl.
*A61B 17/72* (2006.01)
*A61B 17/70* (2006.01)
*A61B 17/00* (2006.01)

(52) U.S. Cl.
CPC .......... *A61B 17/7216* (2013.01); *A61B 17/70* (2013.01); *A61B 2017/00212* (2013.01); *A61B 2017/00221* (2013.01); *A61B 2017/00876* (2013.01); *A61B 2560/02* (2013.01); *A61B 2562/0247* (2013.01)

(58) Field of Classification Search
CPC ............ A61B 17/7216; A61B 17/7225; A61B 17/7014; A61B 17/7016
See application file for complete search history.

(56) References Cited

U.S. PATENT DOCUMENTS

| 2,702,031 A | 2/1955 | Wenger |
| 3,111,945 A | 11/1963 | Von Solbrig |
| 3,372,476 A | 3/1968 | Peiffer |
| 3,377,576 A | 4/1968 | Langberg |

(Continued)

FOREIGN PATENT DOCUMENTS

| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Julianna N Harvey (57) ABSTRACT

The present disclosure broadly provides applications of communication at ultrasound frequencies to establish transcutaneous data communication between medical devices located on and/or within a body of a patient, including inter alia: features for adjustable implants including data communication, hermetic containment, and torque amplification features.

18 Claims, 3 Drawing Sheets

(56) References Cited

U.S. PATENT DOCUMENTS

| | | |
|---|---|---|
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |

(56) References Cited

U.S. PATENT DOCUMENTS

| | | |
|---|---|---|
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |

(56) References Cited

U.S. PATENT DOCUMENTS

| | | |
|---|---|---|
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,393,117 B2 | 7/2016 | Pool |
| 9,398,925 B2 | 7/2016 | Kiester |
| 9,962,199 B2 | 5/2018 | Forsell |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1* | 3/2009 | Dahlgren ............... A61F 2/2445 606/53 |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1* | 11/2009 | Kim ...................... A61B 17/68 606/259 |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |

(56) References Cited

U.S. PATENT DOCUMENTS

| | | |
|---|---|---|
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2011/0301645 A1* | 12/2011 | Connor ............. A61B 17/7016 606/246 |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128868 A1* | 5/2014 | Harrison ............. A61B 17/8004 606/60 |
| 2014/0128920 A1 | 5/2014 | Kantelhardt |
| 2014/0163664 A1 | 6/2014 | Goldsmith |
| 2014/0236234 A1* | 8/2014 | Kroll .................. A61B 17/7083 606/279 |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2016/0183994 A1* | 6/2016 | Quach ................ A61B 17/8866 606/90 |
| 2016/0367297 A1* | 12/2016 | Nill .................... A61B 17/7216 |
| 2017/0333080 A1* | 11/2017 | Roschak ............. A61B 17/68 |
| 2019/0015138 A1* | 1/2019 | Schwardt ........... A61B 17/7216 |
| 2020/0254283 A1 | 8/2020 | Bae et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| JP | 2020049256 A | 4/2020 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™M System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", Sages Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

(56) References Cited

OTHER PUBLICATIONS

Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering•General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.

(56) References Cited

OTHER PUBLICATIONS

Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., "Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", Sages Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.
International Search Report and Written Opinion from corresponding PCT Application No. PCT/US2021/046495 dated Nov. 30, 2021, 17 pages.

\* cited by examiner

REMOTE CONTROL MODULE FOR ADJUSTABLE IMPLANTS

CROSS REFERENCE TO RELATED APPLICATIONS

The present application claims the benefit of U.S. Provisional Application Ser. No. 63/075,640, filed Sep. 8, 2020, which is incorporated by reference in its entirety as though it were fully set forth herein.

FIELD OF DISCLOSURE

The present disclosure pertains to the field of medical devices. More specifically, the present disclosure pertains to remote control modules for adjustable implants.

BACKGROUND

Adjustable medical implants may be used in limb lengthening and/or spinal corrective surgical procedures to treat various conditions such as limb deformities and scoliosis. Typically, these adjustable medical implants are secured to one or more bone portions and gradually adjusted over time until some desired patient outcome is achieved.

These adjustable implants and procedures do not include an accurate and non-invasive means of measurement of in vivo conditions, such as forces and pressures, present at the implant site. Particularly, after the implant is implanted and during the course of treatment.

Further, these adjustable implants and procedures do not include reliable transcutaneous communication devices or methods to achieve bidirectional communication of power/data between implants and other medical devices. This limits biofeedback and control limiting the ability of practitioners to readily understand conditions of implants on and within the body of the patient.

SUMMARY

In one aspect, the present disclosure provides a remote control module for adjustable implants, including: a transceiver configured to send and receive data and a driver configured to adjust an adjustable implant.

In one aspect, the present disclosure provides a system for treating a deformity, including: an adjustable implant; a remote control module; and an external transceiver; wherein the external transceiver is configured to transmit treatment instructions to the remote control module, and wherein the remote control module is configured to adjust the adjustable implant in accordance with the treatment instructions.

In one aspect, the present disclosure provides a method for treating a deformity, including the steps: providing an adjustable implant within an intramedullary cavity of a bone; securing a control module to the bone; communicating adjustment instructions to the control module using an external transceiver; and adjusting the adjustable implant in accordance with the treatment instructions using the control module.

BRIEF DESCRIPTION OF THE DRAWINGS

These and other features may be further understood by those with skill in the art upon a review of the appended drawings, wherein.

DETAILED DESCRIPTION

For purposes of explanation and not limitation, details and descriptions of certain embodiments are hereinafter provided such that one having ordinary skill in the art may be enabled to practice the subject matter. These details and descriptions are representative only of certain embodiments, and a myriad of other embodiments which will not be expressly described will be readily understood by those having skill in the art upon a thorough review hereof. Accordingly, any reviewer of the instant disclosure should interpret the scope of this disclosure by the claims, and such scope shall not be limited by the embodiments described and illustrated herein.

In one aspect, the present disclosure provides a remote control module for adjustable implants. The remote control module provides local control of an adjustable implant. In some embodiments, the remote control module may provide autonomous control and automatic adjustment of the adjustable implant in accordance with instructions communicated to the remote control module by an external transceiver.

The remote control module may include one or more of: a transceiver configured to send and receive data and a driver configured to adjust an adjustable implant. The remote control module may be configured for subcutaneous placement and implantation on and within a body of a patient. For example, the control module may be configured to be secured to a bone of a patient by one or more bone screws in proximity to and/or adjacent to a location of the adjustable implant.

The driver of the remote control module may include a magnetic element configured to magnetically couple with and drive a magnetic element of an adjustable implant. In some embodiments the magnetic element of the remote control module may include an electromagnet configured to generate a rotating magnetic field with the adjustable implant including a rotatable permanent magnet. Rotation of the rotatable permanent magnet by the driver may change a dimension of the adjustable implant.

In some embodiments, the magnetic element of the remote control module may include a first rotatable permanent magnet configured to generate a rotating magnetic field upon a rotation thereof by an actuator. The adjustable implant may also include a second rotatable permanent magnet configured to change a dimension of the adjustable implant upon a rotation thereof. The first rotatable permanent magnet of the remote control module may be magnetically coupled to the second rotatable permanent magnet of the adjustable implant, and the driver may include an actuator configured to rotate the first rotatable permanent magnet. The actuator may include for example an electric motor configured to rotate the first permanent magnet and in turn drive a rotation of the second rotatable permanent magnet thereby adjusting the adjustable implant.

The transceiver of the remote control module may include any communication device configured to communicate information from the remote control module to an external transceiver. Although embodiments of the disclosure are described herein with reference to particular forms of acoustic signal communication, e.g., ultrasonic communication, the communication may be achieved using any form of acoustic signaling including, for example: one or more of an RF signal, a vibrational signal, an infrasound signal, and an ultrasound signal. In certain cases, the acoustic signal(s) are communicated across one or more frequency bands, amplitudes, and/or sound pressure levels (SPLs) suitable for communication with the remote control module.

Bidirectional ultrasonic communication in medical implants may provide power, enhanced control, and biofeedback between the remote control module and other devices located on and within the body of the patient. In some embodiments, the transceiver of the remote control module includes an ultrasonic transducer configured to send and receive ultrasound signals. The remote control module may include a controller operably connected to one or more of the transceiver and the driver. The controller may include one or more of a microcontroller and a microcomputer, and the controller may be configured to interpret signals from the transceiver and drive the driver in accordance with adjustment instructions conveyed from the transceiver.

Information may be conveyed within the body of an organism, such as a human, in radio frequency (RF) signals, which utilize electromagnetic waves. However, RF signals experience large amounts of attenuation in aqueous tissues, and largely reflect off metallic surfaces. Ultrasound waves and ultrasound signals experience much less attenuation within the body, but may experience elevated level of reflection and attenuation in bone and across metals.

The ultrasound waves can convey information via known amplitude and phase shifting techniques. Phase-Shift Keying is a digital modulation process which conveys data by changing the phase of a constant frequency carrier wave. The modulation is accomplished by varying the sine and cosine inputs at a precise time. It is widely used for wireless LANs, RFID and BLUETOOTH (BT). Binary phase-shift keying (BPSK) or any modulation technique may be used in ultrasound communication including: On-Off Keying (OOK), Amplitude-Shift Keying (ASK) and Frequency-Shift Keying (FSK).

The frequency of ultrasound sound waves chosen to establish the bidirectional ultrasonic communication in implants may be in any frequency of ultrasound, and are generally greater than 20 kilohertz. In some embodiments, the frequency of ultrasound sound waves may be between 200 and 400 kilohertz, for example: about 300 kilohertz. Utilizing ultrasound sound waves for power and/or data transmission in medical implants may be beneficial in that (1) ultrasound sound waves have favorable propagation and less attenuation characteristics than RF through metal or solid mediums (e.g., metallic medical implants), and (2) ultrasound sound waves can transmit data transcutaneously through various aqueous tissues in animals (e.g. human skin, muscle and bone).

Once a bidirectional ultrasound communication link is established, the implant may have a power consumption of between 0.5 mW and 80 mW, 1 mW and 60 mW, and 2.0 mW and 40 mW, 10 mW, 5 mW, and any subrange thereof. The ultrasound transducer may consume about 20 mW of power when in operation. The transducer may be configured to transmit data through at least four inches of water or aqueous tissues at a rate of 5 values per second (lkb/s) with a data reliability of 95%. Data reliability transmitted from the transducer at these power levels may be at least 95%, at least 98%, at least 99%, at least 99.9%, or 100%. "Data reliability" means reliability over 10 minutes as calculated from a bit error rate (BER).

As discussed above ultrasound signals experience elevated levels of attenuation and reflection in bone tissues. Providing the remote control module allows a system to take full advantage of the favorable transmission characteristics of ultrasound signals by providing the control module locally and outside of a bone. Also, ultrasound communication and control elements may be bulky and too large to provide in the adjustable implant itself. Providing the remote control module locally outside of the bone, allows a designer to minimize the foot print of the adjustable implant and maximize the communication capabilities of the overall system.

For example, in intramedullary nails the footprint is limited by the size of a bone of the patient. Therefore, it is beneficial to reduce the required footprint of the intramedullary nail but still necessary to provide the communications capabilities. By providing a remote control module locally, the remote control module can drive the intramedullary nail locally and communicate with an external adjustment device.

Figure 1:
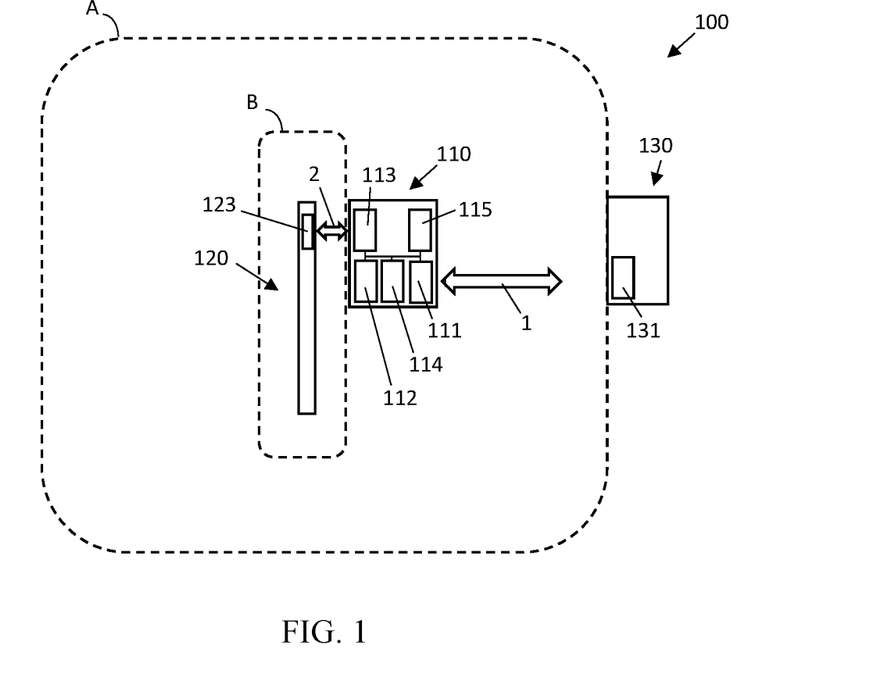
FIG. 1 shows a system in accordance with a first embodiment including a remote control module, an adjustable implant, and an external transceiver configured to communicate with one or more of the remote control module and the adjustable implant.

FIG. 1 shows a schematic diagram of a system 100 including an adjustable implant 120 disposed within a bone B of a patient A, a remote control module 110, and an external transceiver 130 configured to communicate with one or more of the remote control module 110 and the adjustable implant 120.

The remote control module 110 is configured to cause adjustment of the adjustable implant 120 and for transcutaneous data communication with at least the external transceiver 130. The remote control module 110 may include operatively connected circuitry including at least one transceiver 111, a sensor 112, an implant adjustment mechanism 113, a power storage device 114, a controller 115, and interconnects (not shown).

The implant adjustment mechanism 113 can include at least one rotatable permanent magnet or an electrical coil. Where the implant adjustment mechanism 113 includes at least one rotatable permanent magnet, rotation of the rotatable permanent magnet generates a magnetic field that interacts with a magnet within the adjustable implant 120 to cause adjustment of the adjustable implant 120 as will be described herein. Where the actuator 113 includes an electrical coil, the energizing of the coil creates a magnetic field that interacts with the magnet within the adjustable implant 120 to cause adjustment of the adjustable implant 120.

The controller 115 may be any type of controller including: high performance microcontrollers (MCUs), Programmable System on Chip (PSoC), Application Specific Integrated Circuit (ASIC) and any other type of controller and microcomputer. The controller 115 may be disposed on a printed circuit board which may also contain other electronic circuitry and connect other electrical components including: Analog to Digital Converter (ADC), Digital to Analog Converter (DAC), op-amps, memory, phase shifters, and any other electrical component. The controller 115 may further include a frequency synthesizer (i.e., creates carrier waves for transceivers), power amplifiers and noise filters (i.e., conditions carrier wave), power and read strain gauge (i.e., force sensor controls), and may be configured to adjust carrier waves, power, etc., such as by computer executable instructions.

In some embodiments, an energy storage device 114 may be provided. The energy storage device 114 may include a battery, a capacitor, and any other electronic charge or power storage device. The energy storage device 114 may include a rechargeable battery (e.g. Lithium ion rechargeable battery). The power storage device 114 may include a solid state battery and any battery having any known mechanism or battery chemistry. Compliance with national/regional regulatory bodies may play a part in choosing an optimal power storage device for medical implants.

The remote control module 110 may include a charging circuit operably connected to one or more of the power storage device 114 and the transceiver 111. The charging circuit may be integrated into one or more of the controller 115 and the printed circuit board. The charging circuit may include a digital switch wherein upon receiving a modulated signal at a first activation frequency the electronic switch is configured to enable charging of the power storage device 114 with electrical energy harvested by the transceiver 111. The power storage device 114 may be operably connected to the controller 115 via one or more of: wires, boards, and interconnects.

In some embodiments, known wireless charging circuits and techniques including inductive coupling and magnetic coupling may be used to wirelessly transfer power to the remote control module 110. In some embodiments one or more of data and power transfer is achieved using ultrasound signals or RF signals.

In some embodiments, the external transceiver 130 may activate the circuitry of the remote control module 110 by transmitting a modulated signal 1 to the transceiver 111. In some embodiments the modulated signal 1 is an ultrasound signal. The ultrasound signal may be received by the transceiver 111 which may include one or more ultrasonic transducer configured to convert the ultrasound signal into electrical energy. In other embodiments, the modulated signal 1 is a radiofrequency (RF) signal and the transceiver 111 may include an RF transceiver configured to convert RF energy into electrical energy. The controller 115 of the remote control module 110 may be programmed such that upon receipt of an ultrasound or RF signal (as the case may be) corresponding to a particular modulated signal, for example a particular step function of a particular temperance, the controller 115 will open/close an electrical switch and activate the remote control module 110 and place the remote control module 110 in an active and awake state. Similarly, in other embodiments a particular step function may be used to open/close the electrical switch to deactivate the remote control module 110 from the awake state to conserve power of the power storage device.

In some embodiments, the controller 115 may be programmed to time out after a certain period of time, for example if the transceiver 111 has not sent or received signals for a set period of time.

In some embodiments, the controller 115 may be programmed to turn off the power storage device 114 and to put the remote control module 110 to sleep for a certain period of time to conserve power. For example, the controller 115 may activate the remote control module 110 to transmit ultrasonic signals with 25% duty cycle. Between the pulse width, the remote control module 110 is said to be active or in awake state. The controller 115 may deactivate the remote control module 110 during the rest of the period. This state is said to be deactivated or in a sleep state.

In some embodiments the remote control module 110 may include one or more sensors 112 operably connected to the controller 115. The sensors 112 may be designed to measure one or more of: temperature, force, pressure, capacitance, resistance, and any other physical property or characteristic of the adjustable implant 120 or measure information indicative of a biological condition from surrounding anatomical structures of the patient A. The sensor 112 may include for example: a position sensor, an optical sensor, a force sensor, and any known sensor. In the instant embodiment the sensor 112 may be configured to sense force for example.

The sensor 112 may communicate a sensor reading to the controller 115, which may convert the reading to a modulated electrical signal. The modulated electrical signal may then be used to drive the transceiver 111, which then transmits a signal 1 at a frequency corresponding to the modulated electrical signal.

The controller 115 may change analogue information from the sensor 112 to digital values and may drive modulation of the transceiver 111, to transmit data using for example modulated ultrasound waves or RF signals.

The adjustable implant 120 may include any type of adjustable implant. By way of example, the adjustable implant 120 may include magnetically adjustable systems, such as the PRECICE® or MAGEC® magnetically adjustable implant systems for spinal and limb lengthening procedures sold by NuVasive, Inc. of San Diego, California. Such adjustable systems are disclosed in, for example, U.S. Pat. Nos. 9,398,925 and 9,393,117, which are incorporated by reference herein in their entireties. Further, another example of an adjustable implant 110 may include an extramedullary limb lengthening implant.

For example, the actuator of these embodiments may include a second rotatable permanent magnet 123 connected to a lead screw (not shown). Upon an axial rotation of the second rotatable permanent magnet 123 by an externally applied rotating magnetic field (e.g., a magnetic field generated by the actuator 113 of the remote control module 110), the lead screw will rotate. Rotation of the lead screw will cause an axial distraction of the adjustable implant 120, and thereby change a dimension of the adjustable implant 120.

The external transceiver 130 may include at least one ultrasonic transducer 131, including some embodiments with multiple ultrasonic transducers forming an array. A one dimensional array has multiple ultrasonic transducers disposed in a column. Each ultrasonic transducer of a one dimensional array can be assigned a position relative to their position on the array. A two dimensional array has multiple ultrasonic transducers disposed in a matrix or pattern. Each ultrasonic transducer can be assigned a location relative to two dimensions of the matrix. Each array may be a focal array with two or more of the ultrasonic transducers directed to a focal point.

Where modulated RF signals are used, the external transceiver 130 may include an antenna instead of the transducer 131 for transmitting and receiving RF signals from the transceiver 111 of the remote control module 110.

In one embodiment, a method for treating a deformity, may include the steps: providing an adjustable implant 120 within an intramedullary cavity of a bone or outside the bone (e.g., with adjustable spinal implants or with extramedullary limb lengthening implants); B; securing a control module 110 to the bone B in proximity to and/or adjacent to the adjustable implant 120; communicating adjustment and/or treatment instructions to the control module 110 using an external transceiver 130; and adjusting the adjustable implant 120 in accordance with the adjustment and/or treatment instructions using the control module 110. Such instructions can, for example, include a rate of adjustment of the adjustable implant 120, a length of adjustment of the adjustable implant 120, an amount of time of adjustment of the adjustable implant 120, a set time for the adjustable implant 120 to initiate or stop adjustment, and/or how many times adjustment of the adjustable implant 120 is initiated.

As one with skill in the art may appreciate, the remote control module 110 provides localized control and in some embodiments autonomous control of the adjustable implant 120. The external adjustment device 130, and another tertiary device including for example another implant, may communicate adjustment instructions to the remote control module 110 using one or more of an RF and an ultrasound signal 1. In some embodiments the external adjustment device 130, and another tertiary device including for example another implant, may provide remote power to one or more of the remote control module 110 and the adjustable implant 120.

Figure 2:
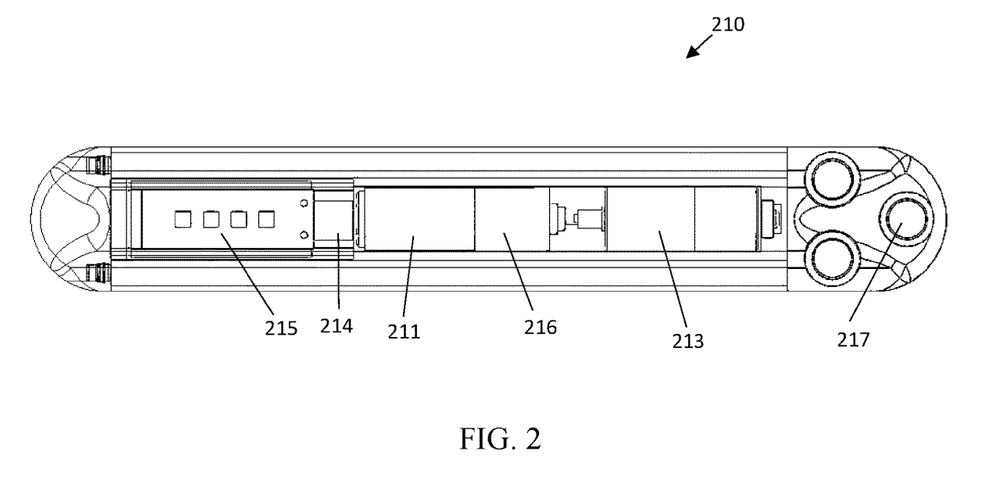
FIG. 2 shows a top view of a remote control module in accordance with a second embodiment.

FIG. 2 shows a top view of a remote control module 210 in accordance with a second embodiment. The control module shown including a controller 215. The controller 215 is operatively connected to one or more of: an ultrasonic transceiver that is contained within or is part of controller 215, an electric motor 211, an energy storage device 214, and an optional gearbox 216. The electric motor 211 is connected to and configured to rotate a first permanent magnet 213 via the gearbox 216. Where the gearbox 216 is not included, the electric motor 211 may be directly coupled with the first permanent magnet 213. The use of the gearbox 216 may be dependent on the system torque requirements.

The remote control module 210 is configured to be mounted on a bone of a patient. The remote control module 210 includes at least one aperture 217 dimensioned to receive at least a portion of an anchor screw (i.e., bone screw) to secure the remote control module 210 to a bone in proximity to and/or adjacent to a location of the adjustable implant 220.

Figure 3:
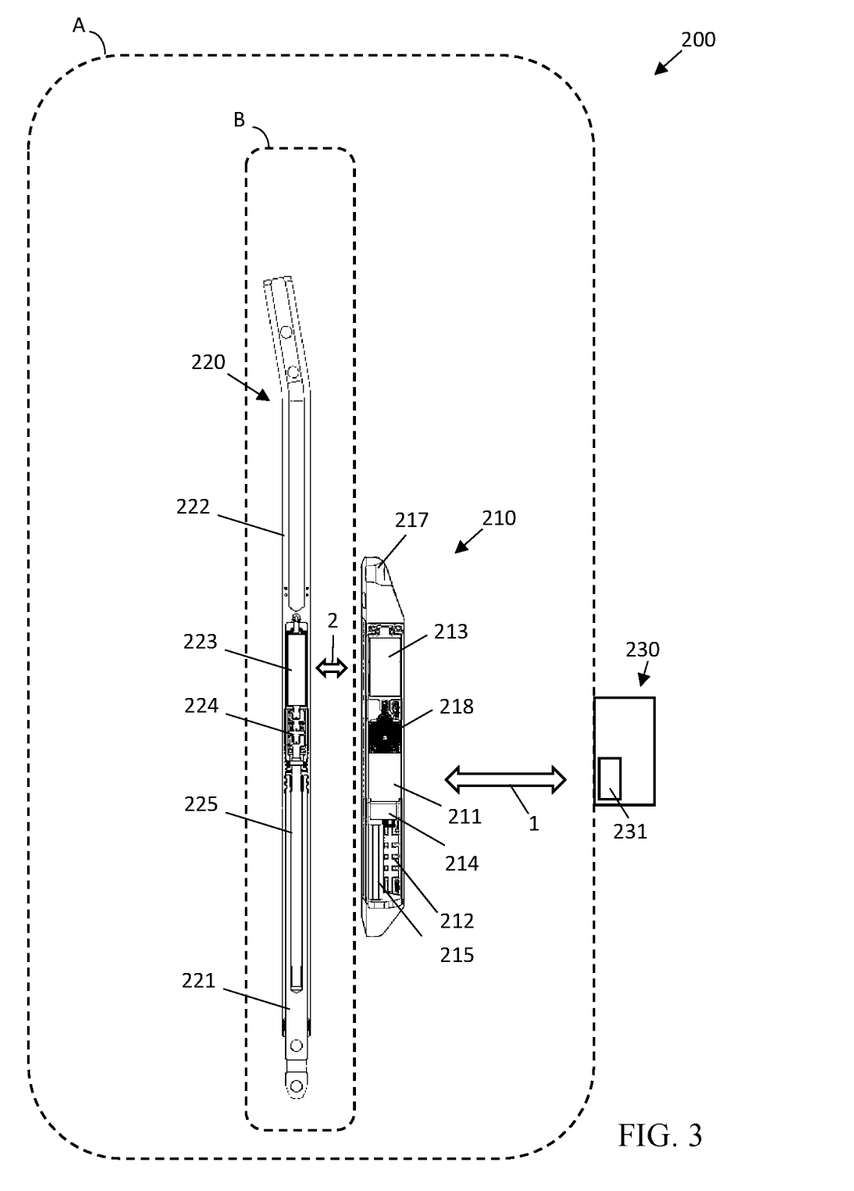
FIG. 3 shows a cross-sectional side view of a system in accordance with a second embodiment including a remote control module, an adjustable implant, and an external transceiver configured to communicate with one or more of the remote control module and the adjustable implant.

FIG. 3 shows a system 200 for treating a deformity in accordance with a second embodiment, the system 200 including a remote control module 210 and an external transceiver 230 each configured for bi-directional ultrasonic data communication. The remote control module 210 includes an actuator or electric motor 211 operatively coupled to a controller 215 and an ultrasonic transducer 212. The remote control module 210 is configured to communicate with the external transceiver 230, and the external transceiver 230 is configured to transmit adjustment instructions to the remote control module 210. The remote control module 210 is also configured to transmit data back to the external transceiver 230.

The adjustable implant 220 is shown disposed in a bone B of a patient A in a first retracted configuration with at least a portion of a rod 221 telescopically received within an outer housing 222. In this embodiment, the adjustable implant 220 is an intramedullary rod configured to treat a bone of a patient.

The remote control module 210 includes a first rotatable permanent magnet 213 configured to magnetically couple 2 with a second rotatable permanent magnet 223 of the adjustable implant 220, wherein as the first rotatable permanent magnet 213 of the remote control module 210 is rotated by the actuator or electric motor 211, the second rotatable permanent magnet 223 will be rotated thereby adjusting the adjustable implant 220.

The rod 221 of the adjustable implant 220 is configured to be telescopically received in and displaced from the outer housing 222 by a rotation of the second rotatable permanent magnet 223. In some embodiments, this adjustable implant 220 may be configured to treat another skeletal deformity, for example a distraction rod configured to be mounted to a plurality of vertebrae and configured to treat scoliosis.

As shown, the outer housing 222 and the rod 221 include apertures dimensioned to receive bone fixation devices there through, with the bone fixation devices configured to secure the implant 220 to at least one bone portion of a patient. The bone fixation devices may include bone screws, hooks, pins, rods, and any device known and used to secure an implant with respect to a patient's skeletal structure.

In this embodiment, the rod 221 includes a cavity having an at least partially threaded interior surface configured to communicate with a lead screw 225. The at least partially threaded interior surface may include a thread disposed directly on an interior surface of the rod 221. Alternatively, a nut may be positioned between the lead screw 225 and the rod 221 such that the nut is secured, e.g., via an adhesive, to the inner surface of the rod 221 and configured to engage with the threads of the lead screw 225.

The lead screw 225 is configured to rotate and displace the rod 221 relative to outer housing 222 upon a rotation of the lead screw 225 by the rotation of the second rotatable permanent magnet 223. As one with skill in the art may appreciate, depending upon the direction of rotation of the lead screw 225, the lead screw 225 may move the rod 221 into or out of the outer housing 222.

The second rotatable permanent magnet 223 is operably connected to a gear housing 224 which may include one or more planetary gear set configured to transfer rotational motion from the second rotatable permanent magnet 223 to the lead screw 225. The one or more planetary gear set may step up or step down the torque of the rotatable permanent magnet 223 depending on the intended application. In other embodiments (not shown), the second rotatable permanent magnet 223 can be directly secured to the lead screw 225 via a pin extending through an aperture within the lead screw 225 and an aperture within a magnet cup or housing surrounding the second rotatable permanent magnet 223. However, it is to be understood that the lead screw 225 and the second rotatable permanent magnet 223 can be coupled via other coupling means known in the art.

In some embodiments the lead screw 225 may include a thread pitch chosen and configured to minimize an amount of energy consumed by the electric motor 211 to move the rod 221 relative to the outer housing 222. In some embodiments, the pitch of the lead screw 225 may be chosen to optimize efficiency of the electric motor 211. Efficiency determines an amount of power consumption and indirectly defines a size of the energy storage device 214. Maximizing lead screw 225 efficiency minimizes power consumption and enabling use of a smaller energy storage device 214.

In this embodiment, a lead screw pitch of 20 threads per inch (tpi) is chosen for the small diameter lead screw 225. A lead screw pitch of 20 tpi is four times more efficient than for example a lead screw pitch of 80 tpi. The pitch of the lead screw can include any pitch known and used in the art, and may be chosen to maximize efficiency of the actuator. In some embodiments, one or more of roller screw threads and ball screw threads may be incorporated into the design to improve lead screw 225 efficiency.

In this embodiment the actuator of the remote control module 210 is an electric motor 211. The electric motor 211 is operably coupled to a controller 215. The controller 215 is also operably coupled to an ultrasonic transducer 212 and an energy storage device 214. The ultrasonic transducer 212 in this embodiment includes a hollow cylindrical ultrasonic transducer. The controller 215 may include a printed circuit board and may be configured for integration in a stacked configuration relative to the ultrasonic transducer 212 and the energy storage device 214, with the electrical connections being established through a chassis via interconnects.

One or more of the energy storage device 214 and the electric motor 211 may be hermetically sealed within the remote control module 210, and may further contained within a sealed container.

The controller 215 is configured to monitor current draw of the electric motor 211 to determine an amount of force applied by the adjustable implant 220. In this embodiment, the controller 215 may monitor the current draw of the electric motor 211 and determine an amount of force being applied to the bone B of the patient A, by monitoring the amount of current drawn by the electric motor 211 to rotate the first rotatable permanent magnet 213 in its coupled state with the second rotatable permanent magnet 223. The controller 215 may communicate the amount of force being applied to the external transceiver 230 using the ultrasonic transducer 212. And the external transceiver 230 and/or a tertiary device may use this information to calculate new distraction instructions for the adjustable implant 220 and communicate the new distraction instructions to the remote control module 220 using an ultrasonic signal 1.

Note, that some embodiments may include some of the same features as other embodiments. Accordingly, similar components share similar reference numbers with the hundreds digit changed to correspond to a specific illustrated embodiment. As one with skill in the art may appreciate, and unless noted otherwise, shared components may not be introduced in every embodiment but are identifiable by their reference numbers in similar embodiments.

Various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present processes, machines, manufacture, composition of matter, means, methods, or steps, presently existing or later to be developed that perform the function or achieve the result as the corresponding embodiments described herein may be utilized according to the present disclosure.

What is claimed is:

1. A deformity treatment system, comprising:
   a control module having a transceiver configured to send and receive data; and
   an adjustable implant, the adjustable implant includes a driver configured to adjust the adjustable implant;
   wherein the adjustable implant includes a first magnetic element;
   wherein the control module is implantable separately from the adjustable implant and includes a second magnetic element; and
   wherein the adjustable implant is adjusted in accordance with treatment instructions using a magnetic field generated from the second magnetic element in the control module to move the first magnetic element in the adjustable implant.

2. The system of claim 1, wherein the driver includes the first magnetic element.

3. The system of claim 2, wherein the driver includes an actuator configured to rotate the magnetic element.

4. The system of claim 3, wherein the first magnetic element includes a rotatable permanent magnet.

5. The system of claim 3, wherein the actuator includes an electric motor.

6. The system of claim 1, wherein the transceiver includes an ultrasonic transducer configured to send and receive ultrasound signals.

7. The system of claim 1, further comprising:
   a controller operably connected to one or more of the transceiver and the driver.

8. The system of claim 7, wherein the controller includes a microcontroller.

9. The system of claim 1, wherein the control module is configured for subcutaneous placement within a body of a patient.

10. The system of claim 1, wherein the control module is configured to be secured to a bone of a patient.

11. A system for treating a deformity, comprising:
    an adjustable implant;
    a control module implantable separately from the adjustable implant, the control module having a magnetic element; and
    an external transceiver;
    wherein the adjustable implant includes a rotatable permanent magnet,
    wherein the rotatable permanent magnet of the adjustable implant is configured to magnetically couple with the magnetic element of the control module,
    wherein the external transceiver is configured to transmit treatment instructions to the control module, and wherein the control module is configured to adjust the adjustable implant in accordance with the treatment instructions, and
    wherein rotation of the rotatable permanent magnet is configured to change a dimension of the adjustable implant.

12. The system of claim 11, wherein the control module includes:
    a transceiver configured to communicate with the external transceiver; and
    a driver configured to adjust an adjustable implant.

13. The system of claim 12, wherein the driver includes an actuator configured to rotate the rotatable permanent magnet of the adjustable implant.

14. The system of claim 11, wherein the external transceiver is configured to communication with the control module using an ultrasound signal.

15. The system of claim 11, wherein the external transceiver is configured to communicate with the control module using a radio frequency signal.

16. The system of claim 11, wherein the control module is configured to determine an amount of adjustment of the adjustable implant and communicate the amount of adjustment to the external transceiver.

17. The system of claim 11, wherein the control module is configured for subcutaneous placement and configured to be secured to a bone of a patient.

18. A method for treating a deformity, comprising:
    providing an adjustable implant within an intramedullary cavity of a bone, wherein the adjustable implant includes a first magnetic element;
    securing a control module to the bone, the control module being implanted separately from the adjustable implant and having a second magnetic element; and
    communicating treatment instructions to the control module using an external transceiver; and
    adjusting the adjustable implant in accordance with the treatment instructions using a magnetic field generated from the second magnetic element in the control module to move the first magnetic element in the adjustable implant.

\* \* \* \* \*